United States Patent [19]

Wong et al.

[11] Patent Number: 5,532,250
[45] Date of Patent: Jul. 2, 1996

[54] POTENTIATION OF DRUG RESPONSE

[75] Inventors: David T. Wong; Juan I. Oguiza, both of Indianapolis, Ind.

[73] Assignee: Eli Lilly and Company, Indianapolis, Ind.

[21] Appl. No.: 442,609

[22] Filed: May 17, 1995

Related U.S. Application Data

[63] Continuation of Ser. No. 277,460, Jul. 19, 1994, abandoned, which is a continuation-in-part of Ser. No. 260,857, Jun. 16, 1994, abandoned.

[51] Int. Cl.$^6$ .......................... H61K 31/38; H61K 31/40
[52] U.S. Cl. ................ 514/415; 514/211; 514/224.2; 514/230.5; 514/249; 514/256; 514/259; 514/312; 514/367; 514/373; 514/375; 514/394; 514/406; 514/418; 514/432; 514/438; 514/443; 514/620; 514/624; 514/650; 514/651; 514/652; 514/654
[58] Field of Search ...................... 514/438, 620, 514/651, 211, 224.2, 230.5, 249, 256, 259, 312, 367, 373, 375, 394, 406, 415, 418, 432, 443, 624, 650, 652, 654

[56] References Cited

U.S. PATENT DOCUMENTS

| | | | |
|---|---|---|---|
| 3,155,669 | 11/1964 | Janssen | 546/20 |
| 3,155,670 | 11/1964 | Janssen | 546/20 |
| 3,337,628 | 8/1967 | Crowther et al. | 564/338 |
| 3,466,325 | 9/1969 | Brandstrom et al. | 564/349 |
| 3,471,515 | 10/1969 | Troxler et al. | 548/503 |
| 3,551,493 | 12/1970 | Ruschig et al. | 549/23 |
| 3,960,891 | 6/1976 | Malen et al. | 564/349 |
| 4,314,081 | 2/1982 | Molloy et al. | 564/347 |
| 4,478,836 | 10/1984 | Mouzin et al. | 514/617 |
| 4,761,501 | 8/1988 | Husbands et al. | 564/167 |
| 4,956,388 | 9/1990 | Robertson et al. | 514/651 |
| 4,988,814 | 1/1991 | Abou-Gharbia et al. | 544/295 |
| 5,013,761 | 5/1991 | Beedle et al. | 514/650 |

OTHER PUBLICATIONS

Davidson, et al., *J. Psychopharmacol. Abstracts*, A7 (1994).
Arborelius, et al., *Psychopharmacology (Berlin)*, 114, B14 (1994).
David Bakish, *Can. J. Psychiatry*, 36, 749–750 (1991).
Markovitz, et al., *Am. J. Psychiatry*, 147, 798–800 (1990).
Li, et al., *Biol. Psychiatry*, 36, 300–308 (1994).
Simon, et al., *Neuroreport*, 5, 229–230 (1993).
Maj, et al., *J. Neural. Transm. [Gen Sect]*, 88, 143–156 (1992).
Hjorth, et al., *Eur. J. Pharmacol.*, 260, 251–255 (1994).
Invernizzi, et al., *Eur. J. Pharmacol.*, 260, 243–246 (1994).
Hjorth, et al., *Neuropharmacology*, 33, 331–334 (1994).
Klimek, et al., *J. Psychiatry Neurosci.*, 19, 63–67 (1994).
Li, et al., *Brain Research*, 630, 148–156 (1993).
Bjorvatn, et al., *Pharmacol. Biochem. Behav.*, 42, 49–56 (1992).
Lesch, et al., *Psychopharmacology (Berlin)*, 105, 415–420 (1991).
Bosker, et al., *Prog. Neuro-Psychopharmacol. & Biol. Psychiat.*, 18, 765–778 (1994).
Cliffe, et al., *J. Med. Chem.*, 36, 1509–1510 (1993).
Moret, et al., *Neuropharmacology*, 24, 1211–1219 (1985).
Middlemiss, et al., *Neuroscience & Biobehavioral Reviews*, 16, 75–82 (1992).
Artigas, *TiPs*, 14, 262 (1993).
Fuller, *Life Sciences*, 55, 163–167 (1994).
Jacobsen, *J. Clin. Psychiatry*, 52, 217–220 (1991).
Robertson, et al., *J. Med. Chem.*, 31, 1412–1417 (1988).
Hillver, et al, *J. Med. Chem.*, 33, 1541–1544 (1990).
Moreau, et al, *Brain Research Bulletin*, 29, 901–904 (1992).
Hjorth, *Journal of Neurochemistry*, 60, 776–779 (1993).
Artigas, et al., *Arch. Gen. Psychiatry*, 51, 248–251 (1994).
Invernizzi, et al, *Brain Research*, 584, 322–324 (1992).
Tang, et al., *Psychiatry Research*, 33, 101–106 (1990).

*Primary Examiner*—Richard L. Raymond
*Attorney, Agent, or Firm*—Joseph A. Jones; David E. Boone

[57] ABSTRACT

The power of fluoxetine, venlafaxine, milnacipran and duloxetine to increase the availability of serotonin, norepinephrine and dopamine, particularly serotonin, is augmented by administration in combination with a drug which is a serotonin 1A receptor antagonist.

21 Claims, No Drawings

POTENTIATION OF DRUG RESPONSE

CROSS-REFERENCE

This application is a continuation of application Ser. No. 08/277,460, filed on Jul. 19, 1994, now abandoned which is a continuation-in-part of application Ser. No. 08/260,857, filed Jun. 16, 1994, now abandoned.

FIELD OF THE INVENTION

The present invention belongs to the fields of pharmacology, medicine and medicinal chemistry, and provides a method and compositions for increasing the availability of serotonin, norepinephrine and dopamine in the brain of patients to whom is administered fluoxetine, venlafaxine, milnacipran or duloxetine.

BACKGROUND OF THE INVENTION

Over the past twenty years or more, the science of pharmacology has been particularly interested in the physiology of the neurons containing monoamines in the human brain. Discovery has followed discovery in the field and it has now been demonstrated that serotonin, norepinephrine and dopamine interact with a great number of receptors in the brain and control or affect processes which regulate many bodily organs and functions. Serotonin, particularly, has been found to be the key to a large number of processes which reveal themselves in both physiological and psychological functions.

Perhaps the most dramatic discovery in medicinal chemistry in the recent past is fluoxetine, a serotonin reuptake inhibitor, which is extremely effective in the treatment of depression. As a reuptake inhibitor, it increases the availability of serotonin in the synapse by reducing the uptake of serotonin by the serotonin uptake carrier. Dysfunction of the serotonin neurons resulting from excessive uptake results in depression, as well as other pathologies of the central nervous system. Not only is fluoxetine spectacularly effective in depression, it is also effective in treating numerous other conditions.

A next generation drug is duloxetine, which is a reuptake inhibitor of both serotonin and norepinephrine. It is now in advanced clinical trials in the treatment of both depression and urinary incontinence, and is a very effective drug. Venlafaxine and milnacipran are also reuptake inhibitors of both serotonin and norepinephrine.

While the primary activity of fluoxetine is the inhibition of the reuptake of serotonin, the cascade of monoamine processes in the brain connects serotonin with both norepinephrine and dopamine. Thus, the increase of availability of serotonin results in increased availability of norepinephrine and dopamine as well. Similarly, the inhibition of the uptake of serotonin and norepinephrine by duloxetine, as well as venlafaxine and milnacipran, also increases dopamine availability.

The present invention provides a method for increasing the availability of serotonin, norepinephrine and dopamine, even compared to the usual increased availability caused by fluoxetine, venlafaxine, milnacipran and duloxetine, by potentiating the action of those drugs.

SUMMARY OF THE INVENTION

The invention provides a method for potentiating the action of a first component chosen from the group consisting of fluoxetine, venlafaxine, milnacipran, and duloxetine in increasing the availability of serotonin, norepinephrine and dopamine in the brain, comprising administering a first component in combination with a second component chosen from the group consisting of alprenolol, WAY 100135, spiperone, pindolol, (S)-UH-301, penbutolol, propranolol, tertatolol, and a compound of the formula

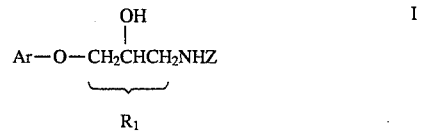

wherein Ar is

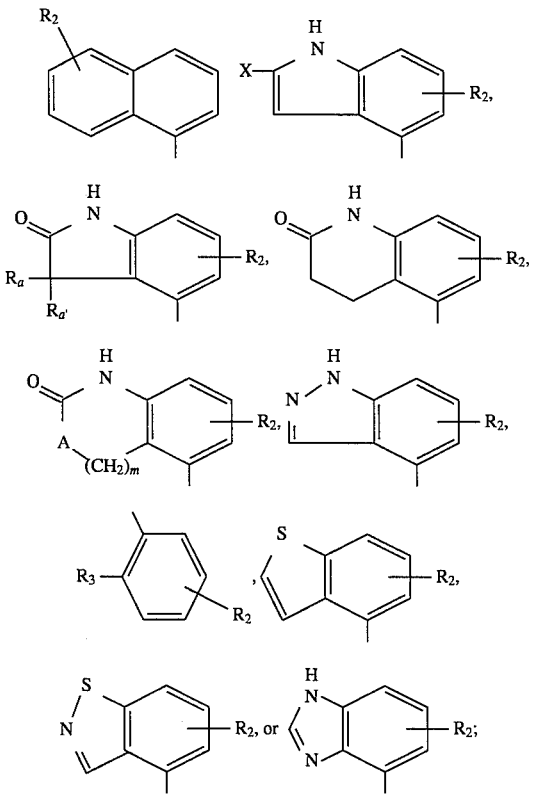

$R_1$ is an optional methyl group substituted on one of the three connecting carbon atoms;

$R_2$ is hydrogen, $C_1$–$C_4$ alkyl, trifluoromethyl, hydroxy, ($C_1$–$C_4$ alkyl)—O—, ($C_1$–$C_4$ alkyl)—S(O)$_p$—, or halo;

$R_3$ is $C_3$–$C_8$ cycloalkyl or a bicycloalkyl group of the formula

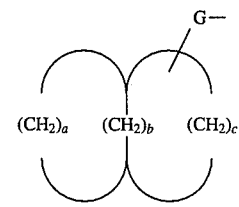

where a and c are independently 1–5, b is 0–5, and (a+c) is greater than 2;

z is a straight or branched $C_4$–$C_{10}$ alkane, alkene, or alkyne group; ($C_4$–$C_8$ cycloalkyl) optionally substituted with $C_1$–$C_4$ alkyl or phenyl; a bicycloalkyl group of the formula

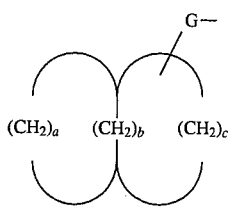

wherein a and c are independently 1–5, b is 0–5, and (a+c) is greater than 2; optionally phenyl substituted $C_2$–$C_{10}$ alkyl where the phenyl group can be optionally substituted with $R_2$ as previously defined; or ($C_1$–$C_4$ alkylidene)—T—($C_1$–$C_4$ alkyl), where T is —O—, —S—, —SO—, or —$SO_2$—;

where each G is independently a bond or $C_1$–$C_4$ alkylidene;

X is —H, —COY, —CN, or $C_1$–$C_4$ alkyl;

Y is —OH, —O—($C_1$–$C_4$ alkyl), or —$NH_2$;

$R_a$ and $R_{a'}$ are independently hydrogen or $C_1$–$C_3$ alkyl, or when taken together with the carbon atom to which they are attached form a $C_3$–$C_8$ cycloalkyl ring;

p is 0, 1, or 2;

A is —O—, —S—, —NH—, or —$NCH_3$—; and m is 0, 1, 2, or 3; or a pharmaceutically acceptable salt thereof.

The invention also provides pharmaceutical compositions which comprise a first component in combination with one of the second component compounds named above. Further, it provides methods of treating a pathological condition which is created by or is dependent upon decreased availability of serotonin, dopamine or norepinephrine, which comprise administering to a patient in need of such treatment an adjunctive therapy comprising a first component and one of the compounds named above.

Still further, the invention provides a preferred manner of carrying out the above method of adjunctive therapy wherein the second component is administered in a manner which provides a substantially constant blood level of the second component, which level is sufficient to provide a substantially constant degree of potentiation of the action of the first component. Compositions adapted for carrying out the preferred manner of the invention are also provided.

DESCRIPTION OF THE PREFERRED EMBODIMENTS

In this document, all temperatures are described in degrees Celsius, and all amounts, ratios of amounts and concentrations are described in weight units unless otherwise stated.

The Compounds

Fluoxetine, N-methyl-3-(p-trifluoromethylphenoxy)-3-phenylpropylamine, is marketed in the hydrochloride salt form, and as the racemic mixture of its two enantiomers. U.S. Pat. No. 4,314,081 is an early reference on the compound. Robertson et al., *J. Med. Chem.* 31, 1412 (1988), taught the separation of the R and S enantiomers of fluoxetine and showed that their activity as serotonin uptake inhibitors is similar to each other. In this document, the word "fluoxetine" will be used to mean any acid addition salt or the free base, and to include either the racemic mixture or either of the R and S enantiomers.

Duloxetine, N-methyl-3-(1-naphthalenyloxy)-3-(2-thienyl)propanamine, is usually administered as the hydrochloride salt and as the (+) enantiomer. It was first taught by U.S. Pat. No. 4,956,388, which shows its high potency. The word "duloxetine" will be used here to refer to any acid addition salt or the free base of the molecule.

Venlafaxine is known in the literature, and its method of synthesis and its activity as an inhibitor of serotonin and norepinephrine uptake are taught by U.S. Pat. No. 4,761,501. Venlafaxine is identified as compound A in that patent.

Milnacipran (N,N-diethyl-2-aminomethyl-1-phenylcyclopropanecarboxamide) is taught by U.S. Pat. No. 4,478,836, which prepared milnacipran as its Example 4. The patent describes its compounds as antidepressants. Moret et al., *Neuropharmacology* 24, 1211–19 (1985), describe its pharmacological activities.

Duloxetine and fluoxetine, as well as the other first components, are known to increase the availability of serotonin (5-HT), dopamine (DA) and norepinephrine (NE), and the second component drugs potentiate that valuable property. The second component drugs have in common the property of being antagonists of the serotonin 1A receptor.

(S)-UH-301 ((S)-5-fluoro-8-hydroxy-2-dipropylaminotetralin) is well known to pharmacologists and pharmaceutical chemists. Hillver et al. taught its synthesis in *J. Med. Chem.* 33, 1541–44 (1990) and Moreau et al., *Brain Res. Bull.* 29, 901–04 (1992) provided considerable in vivo data about the compound.

Alprenolol (1-(1-methylethyl)amino-3-[2-(2-propenyl)phenoxy]-2-propanol) was disclosed by Brandstrom et al., U.S. Pat. No. 3,466,325, which shows its preparation as Example 5.

WAY 100135 (N-(t-butyl)-3-[4-(2-methoxyphenyl)piperazin-1-yl]-2-phenylpropanamide) was disclosed by Abou-Gharbia et al., U.S. Pat. No. 4,988,814, who taught that the compound has affinity for the 5-$HT_1$A receptor. Cliffe et al., *J. Med. Chem.* 36, 1509–10 (1993) showed that the compound is a 5-$HT_1$A antagonist.

Spiperone (8-[4-(4-fluorophenyl)-4-oxobutyl]-1-phenyl-1,3,8-triazaspiro[4,5]decan-4-one) is a well-known compound, taught in U.S. Pat. Nos. 3,155,669 and 3,155,670. Its activity as a 5-$HT_1$A antagonist is shown by Middlemiss et al., *Neurosci, and Biobehav, Rev.* 16, 75–82 (1992).

Tertatolol (8-(3-t-butylamino-2-hydroxypropyloxy)thiochroman) was disclosed by Malen et al., U.S. Pat. No. 3,960,891, which teaches it to be a blocker of cardiac betaadrenergic receptors. Its other activities, including the presently used 5-$HT_1$A antagonist activity, have been discovered since the original patents appeared.

Propranolol (1-isopropylamino-3-(1-naphthalenyloxy)2-propanol) was disclosed by Crowther et al., U.S. Pat. No. 3,337,628 to be a beta-blocker like tertatolol. Again, its other properties are also well known to pharmacologists.

Penbutolol (1-(t-butylamino)-2-hydroxy-3-(2-cyclopentyl-phenoxy)propane) was taught by Rushing et al., U.S. Pat. No. 3,551,493, which describes it as a beta-blocker. Both the (−) and the (+) enantiomers of penbutolol are of interest; the (−) enantiomer is preferred for the present purpose but both enantiomers and the racemic mixture are included in the word "penbutolol" in this document.

Pindolol (4-(2-hydroxy-3-isopropylamino propoxy)indole) was disclosed by Troubler et al., U.S. Pat. No. 3,471,515, which describes this compound as well as a beta blocker. The compound is usually administered as the racemic mixture, but the two enantiomers have been isolated and the (−) enantiomer is preferred if a single isomer product is desired in a given application. Both enantiomers and the racemic mixture are included in the word "pindolol" in this document.

The compounds of formula I are taught by Beetle, et al., U.S. Pat. No. 5,013,761, the description of which is incorporated herein by reference. The synthesis and characteristics, including the $5HT_1A$ antagonist activity, of the compounds is shown in that patent.

The particularly preferred compounds of formula I include, for example, the following individual compounds. It will be understood that the following compounds are typical of those of formula 1 but that the compounds include numerous other valuable species as shown by the previously mentioned U.S. Patent. It will be further understood that, while individual salts, and in some cases, enantiomers, are mentioned below and are of particular interest, other salts, and enantiomers, diastereomers, and racemates, are likewise valuable and are included in formula I as agents for the present invention.

1-(4-indolyloxy)-3-cyclohexylamino-2-propanol, maleate salt;
  cis-1-(4-indolyloxy)-3-(4-phenylcyclohexyl-amino)-2-propanol, oxalate salt;
  1-(4-indolyloxy)-3-(2-phenylethylamino)-2-propanol, oxalate salt;
  1-(4-indolyloxy)-3-(3-phenylpropylamino)-2-propanol, oxalate salt;
  1-(4-indolyloxy)-3-(4-phenylbutylamino)-2-propanol, oxalate salt;
  1-(4-indolyloxy)-3-cyclopentylamino-2-propanol, maleate salt;
  1-(4-indolyloxy)-3-cycloheptylamino-2-propanol;
  (S)-(−)-1-(4-indolyloxy)-3-cyclohexylamino-2-propanol, maleate salt;
  (+)-1-(4-indolyloxy)-3-cyclohexylamino-2-propanol, maleate salt;
  1-(4-indolyloxy)-3-(3-methylcyclohexylamino)-2-propanol;
  1-(4-indolyloxy)-3-(4-methylcyclohexylamino)-2-propanol;
  1-(4-indolyloxy)-3-(5-phenylpentylamino)-2-propanol, oxalate salt;
  1-(4-indolyloxy)-3-(6-phenylhexylamino)-2-propanol, oxalate salt;
  1-(4-indolyloxy)-3-(2,3-dimethylcyclohexyl-amino)-2-propanol, oxalate salt;
  (+−)-1-(4-indolyloxy)-3-(3-pentylamino)-2-propanol;
  (R)-(+)-1-(4-indolyloxy)-3-cyclohexylamino-2-propanol, butanedioate salt;
  (R)-(−)-1-(4-indolyloxy)-3-cyclohexylamino-2-propanol, butanedioate salt;
  1-(2-trifluoromethyl-4-benzimidazolyl)-3-(4-phenylbutylamino)-2-propanol;
  (exo)-1-(4-indolyloxy)-3-(norbornylamino)-2-propanol;
  (endo)-1-(4-indolyloxy)-3-(norbornylamino)-2-propanol;
  1-(1-napthalenyloxy)-3-cycloheptylamino-2-propanol, oxalate salt;
  1-(2-cyclopentylphenoxy)-3-cycloheptylamino-2-propanol, oxalate salt;
  1-(2-cyclohexylphenoxy)-3-cyclooctylamino-2-propanol, oxalate salt;
  1-(2-cycloheptylphenoxy)-3-(1,2,3-trimethyl-2-propylamino)-2-propanol, oxalate salt; and
  1-(2-cyclopropylphenoxy)-3-(1,1-dimethylbutyl-amino)-2-propanol, oxalate salt.

The group of the compounds of formula I wherein the group Ar is indolyl or substituted indolyl constitutes a further preferred class of $5-HT_1A$ antagonists; and the compounds of formula 1 wherein Z is ($C_4-C_8$ cycloalkyl) optionally substituted with $C_1-C_4$ alkyl or phenyl; or Z represents optionally phenyl substituted $C_2-C_{10}$ alkyl where the phenyl group can be optionally substituted with $R_2$; constitute further particularly preferred classes of compounds for use in the present invention.

All of the U.S. patents which have been mentioned above in connection with compounds used in the present invention are incorporated herein by reference.

While all combinations of first component and second component compounds are useful and valuable, certain combinations are particularly valued and are preferred, as follows:

fluoxetine/pindolol
duloxetine/pindolol
fluoxetine/penbutolol
duloxetine/penbutolol
fluoxetine/propranolol
duloxetine/propranolol
fluoxetine/tertatolol
duloxetine/tertatolol
fluoxetine/4-(2-hydroxy-3-cyclohexylaminopropoxy)-indole
duloxetine/4-(2-hydroxy-3-cyclohexylaminopropoxy)-indole In general, combinations and methods of treatment using fluoxetine or duloxetine as the first component are preferred.

It will be understood by the skilled reader that all of the compounds used in the present invention are capable of forming salts, and that the salt forms of pharmaceuticals are commonly used, often because they are more readily crystallized and purified than are the free bases. In all cases, the use of the pharmaceuticals described above as salts is contemplated in the description herein, and often is preferred, and the pharmaceutically acceptable salts of all of the compounds are included in the names of them.

Administration

The dosages of the drugs used in the present invention must, in the final analysis, be set by the physician in charge of the case, using knowledge of the drugs, the properties of the drugs in combination as determined in clinical trials, and the characteristics of the patient, including diseases other than that for which the physician is treating the patient. General outlines of the dosages, and some preferred dosages, can and will be provided here. Dosage guidelines for some of the drugs will first be given separately; in order to create a guideline for any desired combination, one would choose the guidelines for each of the component drugs.

Fluoxetine: from about 1 to about 80 mg, once/day; preferred, from about 10 to about 40 mg once/day; preferred for bulimia and obsessive-compulsive disease, from about 20 to about 80 mg once/day;

Duloxetine: from about 1 to about 30 mg once/day; preferred, from about 5 to about 20 mg once/day;

Venlafaxine: from about 10 to about 150 mg once-thrice/day; preferred, from about 25 to about 125 mg thrice/day;

Milnacipran: from about 10 to about 100 mg once-twice/day; preferred, from about 25 to about 50 mg twice/day;

Pindolol: from about 1 to about 60 mg once-thrice/day; preferred, from about 5 to about 60 mg once-thrice/day; also preferred, from about 1 to about 10 mg twice/day;

Penbutolol: from about 2 to about 80 mg once/day; preferred, from about 10 to about 80 mg once/day; also preferred, from about 2 to about 20 mg once/day;

propranolol: from about 10 to about 240 mg once-twice/day; preferred, from about 10 to about 120 mg twice/day; also preferred, from about 40 to about 240 mg once-twice/day;

4-(2-Hydroxy-3-cyclohexylaminopropoxy)indole: from about 1 to about 50 mg once-twice/day; preferred, from about 1 to about 10 mg twice/day.

In more general terms, one would create a combination of the present invention by choosing a dosage of first component compound according to the spirit of the above guideline, and choosing a dosage of the second component compound in the general range of from about 1 to about 250 mg/dose. More preferred dosages, depending on the compound, would be from about 1 to about 100 mg/dose, and even more preferred dosages would be likely to be found in the range of from about 1 to about 50 mg/dose, ideally from about 1 to about 25 mg/dose.

The adjunctive therapy of the present invention is carried out by administering a first component together with one of the second component compounds in any manner which provides effective levels of the two compounds in the body at the same time. All of the compounds concerned are orally available and are normally administered orally, and so oral administration of the adjunctive combination is preferred. They may be administered together, in a single dosage form, or may be administered separately.

However, oral administration is not the only route or even the only preferred route. For example, transdermal administration may be very desirable for patients who are forgetful or petulant about taking oral medicine. One of the drugs may be administered by one route, such as oral, and the other may be administered by the trans-dermal, percutaneous, intravenous, intramuscular, intranasal or intrarectal route, in particular circumstances. The route of administration may be varied in any way, limited by the physical properties of the drugs and the convenience of the patient and the caregiver.

It is particularly preferred, however, for the adjunctive combination to be administered as a single pharmaceutical composition, and so pharmaceutical compositions incorporating both a first component and a second component compound are important embodiments of the present invention. Such compositions may take any physical form which is pharmaceutically acceptable, but orally usable pharmaceutical compositions are particularly preferred. Such adjunctive pharmaceutical compositions contain an effective amount of each of the compounds, which effective amount is related to the daily dose of the compounds to be administered. Each adjunctive dosage unit may contain the daily doses of both compounds, or may contain a fraction of the daily doses, such as one-third of the doses. Alternatively, each dosage unit may contain the entire dose of one of the compounds, and a fraction of the dose of the other compound. In such case, the patient would daily take one of the combination dosage units, and one or more units containing only the other compound. The amounts of each drug to be contained in each dosage unit depends on the identity of the drugs chosen for the therapy, and other factors such as the indication for which the adjunctive therapy is being given.

The second component compounds, taken as a class, have short lives in the body and, accordingly, provide only short periods of activity following each dose. For example, pindolol is routinely administered twice/day in the prior art, and it has been administered even more often. In the context of the present invention, it is therefore preferred to administer the second component compounds in a manner which supplies a substantially constant blood level of the second component in the body of the patient, at a sufficiently high level to provide a substantially constant degree of potentiation of the action of the first component.

It is not intended, of course, that the present invention or any method of human treatment can provide a truly constant blood level and degree of potentiation. Biological processes always vary and prevent precisely constant results. The term "substantially constant" is used herein to refer to administration resulting in blood levels and degrees of potentiation which are sufficiently constant as to provide continuous improved efficacy over a treatment day, compared to the efficacy of the first component compound alone. Another way to consider substantially constant potentiation is by comparing the availability of serotonin, norepinephrine and dopamine in the brain of the patient. By "substantially constant" in such terms is meant a condition where the peak and the valley of availability differ by no more than about a factor of 2 over the course of a treatment day. Another way to consider "substantially constant" is a condition where the peak and valley differ by no more than about a factor of 1.5; or they differ by no more than a range of from about 1.5 to about 3.

Such administration of the second component may be provided by means known to pharmaceutical scientists. For example, the total daily dosage of a second component may be formulated in a manner which provides a substantially constant flow of compound to the patient. To consider only pindolol, at least the following references teach sustained release formulations: German Patent 3632201, capsules; Swiss Patent 634990, tablets; German Patent 3237945, buccal tape; German Patent 2732335, tablets; U.S. Patent 5260066, cryogels; European Patent Publication 361894, liposomes; Japanese Patent 84-66710, transdermal patches. Pharmaceutical scientists are acquainted in modern practice with the manners of adjusting a sustained release formulation to provide the desired rate of administration of a given compound and such formulations can be prepared by the skill of the pharmaceutical art of the compounds used as second components here.

Such formulations of a second component compound may be combined in a single dosage form with the chosen first component compound. For example, a small tablet or pellets of the second component, formulated to provide constant availability of the compound, may be combined, for example in a capsule, with the first component compound. Alternatively, a transdermal patch may be prepared which has a relatively rapidly releasing area of first component, and a relatively slowly releasing area of second component. Still further, a suspension may be prepared in which the first component is present as particles of pure compound, and the particles of the second component are coated to provide sustained release in the body. In such manners, the availability of the second component may be adjusted to provide the desired substantially constant blood levels and, hence, substantially constant potentiation of the first component. Compositions so adapted for providing substantially constant potention of the first component are preferred compositions of the present invention.

The inert ingredients and manner of formulation of the adjunctive pharmaceutical compositions are conventional, except for the presence of the combination of the first component and the second component compound. The usual methods of formulation used in pharmaceutical science may be used here. All of the usual types of compositions may be used, including tablets, chewable tablets, capsules, solutions, parenteral solutions, intranasal sprays or powders, troches, suppositories, transdermal patches and suspensions. In general, compositions contain from about 0.5% to about 50% of the compounds in total, depending on the desired doses and the type of composition to be used. The amount of the compounds, however, is best defined as the effective amount, that is, the amount of each compound which provides the desired dose to the patient in need of such treatment. The activity of the adjunctive combinations do not depend on the nature of the composition, so the compositions are chosen and formulated solely for convenience and economy. Any of the combinations may be formulated in any desired form of composition. Some discussion of different compositions will be provided, followed by some typical formulations.

Capsules are prepared by mixing the compound with a suitable diluent and filling the proper amount of the mixture in capsules. The usual diluents include inert powdered substances such as starch of many different kinds, powdered cellulose, especially crystalline and microcrystalline cellulose, sugars such as fructose, mannitol and sucrose, grain flours and similar edible powders.

Tablets are prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant is necessary in a tablet formulation to prevent the tablet and punches from sticking in the die. The lubricant is chosen from such slippery solids as talc, magnesium and calcium stearate, stearic acid and hydrogenated vegetable oils.

Tablet disintegrators are substances which swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethylcellulose, for example, may be used, as well as sodium lauryl sulfate.

Enteric formulations are often used to protect an active ingredient from the strongly acid contents of the stomach. Such formulations are created by coating a solid dosage form with a film of a polymer which is insoluble in acid environments, and soluble in basic environments. Exemplary films are cellulose acetate phthalate, polyvinyl acetate phthalate, hydroxypropyl methylcellulose phthalate and hydroxypropyl methylcellulose acetate succinate. It is preferred to formulate duloxetine and duloxetine-containing combinations as enteric compositions, and even more preferred to formulate them as enteric pellets.

A preferred duloxetine enteric formulation is a pellet formulation comprising a) a core consisting of duloxetine and a pharmaceutically acceptable excipient; b) an optional separating layer; c) an enteric layer comprising hydroxypropylmethylcellulose acetate succinate (HPMCAS) and a pharmaceutically acceptable excipient; d) an optional finishing layer. The following example demonstrates the preparation of a preferred such formulation.

EXAMPLE 10 mg Duloxetine base/capsule

Bill of Materials

| Beads | |
|---|---|
| Sucrose-starch nonpareils, | |
| 20–25 mesh | 60.28 mg |
| Duloxetine layer | |
| Duloxetine | 11.21 |
| Hydroxypropylmethylcellulose | 3.74 |
| Separating layer | |
| Hydroxypropylmethylcellulose | 2.51 |
| Sucrose | 5.00 |
| Talc, 500 mesh | 10.03 |
| Enteric layer | |
| HPMCAS, LF grade, Shin-Etsu Chemical Co., Tokyo, Japan | 25.05 |
| Triethyl citrate | 5.00 |
| Talc, 500 mesh | 7.52 |
| Finishing layer | |
| Hydroxypropylmethylcellulose | 8.44 |
| Titanium dioxide | 2.81 |
| Talc | Trace |
| | 141.60 mg |

The duloxetine layer was built up by suspending duloxetine in a 4% w/w solution of the hydroxypropylmethylcellulose in water, and milling the suspension with a CoBall Mill (Fryma Mashinen AG, Rheinfelden, Switzerland) model MS-12. A fluid bed dryer with a Wurster column was used to make this product, at a batch size of 1.0 kg. The separating layer was added from a 4% w/w solution of the hydroxypropyl-methylcellulose in water, in which the sucrose was also dissolved.

In order to prepare the enteric coating suspension, purified water was cooled to 10° C. and the polysorbate, triethyl citrate and silicone emulsion were added and dispersed or dissolved. Then the HPMCAS and talc were added and agitated until homogeneity was obtained, and the HPMCAS was fully neutralized by addition of ammonium hydroxide until solution of the polymer was complete. To this suspension, a carboxymethylcellulose aqueous solution, 0.5% w/w, was added and blended thoroughly. The enteric suspension was maintained at 20° C. during the coating process. The enteric suspension was then added to the partially completed pellets in the Wurster column at a spray rate of about 15 ml/min, holding the temperature of the inlet air at about 50° C.. The product was dried in the Wurster at 50° C. when the enteric suspension had been fully added, and then dried on trays for 3 hours in a dry house at 60° C. A finishing layer was then applied which consisted of a 4.5% w/w/hydroxypropylmethylcellulose solution containing titanium dioxide and propylene glycol as plasticizer. The pellets were completely dried in the fluid bed dryer and then were then filled in size 3 gelatin capsules.

Tablets are often coated with sugar as a flavor and sealant, or with film-forming protecting agents to modify the dissolution properties of the tablet. The compounds may also be formulated as chewable tablets, by using large amounts of pleasant-tasting substances such as mannitol in the formulation, as is now well-established practice. Instantly dissolving tablet-like formulations are also now frequently used to assure that the patient consumes the dosage form, and to avoid the difficulty in swallowing solid objects that bothers some patients.

When it is desired to administer the combination as a suppository, the usual bases may be used. Cocoa butter is a traditional suppository base, which may be modified by addition of waxes to raise its melting point slightly. Water-miscible suppository bases comprising, particularly, polyethylene glycols of various molecular weights are in wide use, also.

Transdermal patches have become popular recently. Typically they comprise a resinous composition in which the drugs will dissolve, or partially dissolve, which is held in contact with the skin by a film which protects the composition. Many patents have appeared in the field recently. Other, more complicated patch compositions are also in use, particularly those having a membrane pierced with innumerable pores through which the drugs are pumped by osmotic action.

The following typical formulae are provided for the interest and information of the pharmaceutical scientist.

Formulation 1

Hard gelatin capsules are prepared using the following ingredients:

|  | Quantity (mg/capsule) |
| --- | --- |
| Fluoxetine, racemic, hydrochloride | 20 mg |
| Pindolol | 30 |
| Starch, dried | 200 |
| Magnesium stearate | 10 |
| Total | 260 mg |

Formulation 2

A tablet is prepared using the ingredients below:

|  | Quantity (mg/capsule) |
| --- | --- |
| Fluoxetine, racemic, hydrochloride | 10 |
| (−)-Penbutolol | 40 |
| Cellulose, microcrystalline | 400 |
| Silicon dioxide, fumed | 10 |
| Stearic acid | 5 |
| Total | 465 mg |

The components are blended and compressed to form tablets each weighing 465 mg.

Formulation 3

An aerosol solution is prepared containing the following components:

|  | Weight |
| --- | --- |
| (+)-Duloxetine, hydrochloride | 10 |
| Pindolol | 10 |
| Ethanol | 25.75 |
| Propellant 22 | 70.00 |
| (Chlorodifluoromethane) | |
| Total | 115.75 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 80 mg of active ingredient, are made as follows:

| (+)-Duloxetine, hydrochloride | 20 mg |
| --- | --- |
| (−)-Penbutolol | 60 mg |
| Starch | 45 mg |
| Microcrystalline cellulose | 35 mg |
| Polyvinylpyrrolidone | 4 mg |
| (as 10% solution in water) | |
| Sodium carboxymethyl starch | 4.5 mg |
| Magnesium stearate | 0.5 mg |
| Talc | 1 mg |
| Total | 170 mg |

The active ingredient, starch and cellulose are passed through a No. 45 mesh U.S. sieve and mixed thoroughly. The aqueous solution containing polyvinyl- pyrrolidone is mixed with the resultant powder, and the mixture then is passed through a No. 14 mesh U.S. sieve. The granules so produced are dried at 50° C. and passed through a No. 18 mesh U.S. Sieve. The sodium carboxymethyl starch, magnesium stearate and talc, previously passed through a No. 60 mesh U.S. sieve, are then added to the granules which, after mixing, are compressed on a tablet machine to yield tablets each weighing 170 mg.

Formulation 5

Capsules, each containing 130 mg of active ingredient, are made as follows:

| Fluoxetine, racemic, hydrochloride | 30 mg |
| --- | --- |
| Propranolol | 100 mg |
| Starch | 59 mg |
| Microcrystalline cellulose | 59 mg |
| Magnesium stearate | 2 mg |
| Total | 250 mg |

The active ingredient, cellulose, starch, and magnesium stearate are blended, passed through a No. 45 mesh U.S. sieve, and filled into hard gelatin capsules in 250 mg quantities.

Formulation 6

Suppositories, each containing 45 mg of active ingredient, are made as follows:

| (+)-Duloxetine, hydrochloride | 5 mg |
| --- | --- |
| Propranolol | 40 mg |
| Saturated fatty acid glycerides | 2,000 mg |
| Total | 2,045 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

13
Formulation 7

Suspensions, each containing 70 mg of active ingredient per 5 ml dose, are made as follows:

| Fluoxetine, racemic, hydrochloride | 10 mg |
| --- | --- |
| Propranolol | 60 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| (+)-Duloxetine, hydrochloride | 10 mg |
| --- | --- |
| Propranolol | 20 mg |
| Isotonic saline | 1,000 ml |

Benefit of the Invention

As stated above, the benefit of the invention is its ability to augment the increase in availability of serotonin, norepinephrine and dopamine caused by the first component compounds, resulting in improved activity in treating the various conditions described below in detail. The increase in availability of serotonin is particularly important and is a preferred aspect of the invention. Further, the invention provides a more rapid onset of action than is usually provided by treatment with fluoxetine or duloxetine alone. The experimental data shown below clearly demonstrate the rapid onset of action, as well as the augmentation of availability of the monoamines.

Preferred pathological conditions to be treated by the present method of adjunctive therapy include depression, obsessive-compulsive disease and obesity. Another preferred condition more specific to combinations including preferably duloxetine but also venlafaxine and milnacipran is urinary incontinence.

Depression in its many variations has recently become much more visible to the general public than it has previously been. It is now recognized as an extremely damaging disorder, and one that afflicts a surprisingly large fraction of the population. Suicide is the most extreme symptom of depression, but millions of people, not quite so drastically afflicted, live in misery and partial or complete uselessness, and afflict their families as well by their affliction. The introduction of fluoxetine was a breakthrough in the treatment of depression, and depressives are now much more likely to be diagnosed and treated than they were only a decade ago. Duloxetine is in clinical trials for the treatment of depression and is likely to become a marketed drug for the purpose.

Depression is often associated with other diseases and conditions, or caused by such other conditions. For example, it is associated with Parkinson's disease; with HIV; with Alzheimer's disease; and with abuse of anabolic steroids. Depression may also be associated with abuse of any substance, or may be associated with behavioral problems resulting from or occurring in combination with head injuries, mental retardation or stroke. Depression in all its variations is a preferred target of treatment with the present adjunctive therapy method and compositions.

Obsessive-compulsive disease appears in a great variety of degrees and symptoms, generally linked by the patient's uncontrollable urge to perform needless, ritualistic acts. Acts of acquiring, ordering, cleansing and the like, beyond any rational need or rationale, are the outward characteristic of the disease. A badly afflicted patient may be unable to do anything but carry out the rituals required by the disease. Fluoxetine is approved in the United States and other countries for the treatment of obsessive-compulsive disease and has been found to be effective.

Obesity is a frequent condition in the American population. It has been found that fluoxetine will enable an obese patient to lose weight, with the resulting benefit to the patient's circulation and heart condition, as well as general well being and energy.

Urinary incontinence is classified generally as stress or urge incontinence, depending on whether its root cause is the inability of the sphincter muscles to keep control, or the overactivity of the bladder muscles. Duloxetine controls both types of incontinence, or both types at once, and so is important to the many people who suffer from this embarrassing and disabling disorder.

The present invention is useful for treating many other diseases, disorders and conditions as well, as set out below. In many cases, the diseases to be mentioned here are classified in the International Classification of Diseases, 9th Edition (ICD), or in the Diagnostic and Statistical Manual of Mental Disorders, 3rd Version Revised, published by the American Psychiatric Association (DSM). In such cases, the ICD or DSM code numbers are supplied below for the convenience of the reader.

depression, ICD 296.2 & 296.3, DSM 296, 294.80, 293.81, 293.82, 293.83, 310.10, 318.00, 317.00 migraine pain, particularly neuropathic pain bulimia, ICD 307.51, DSM 307.51 premenstrual syndrome or late luteal phase syndrome, DSM 307.90 alcoholism, ICD 305.0, DSM 305.00 & 303.90 tobacco abuse, ICD 305.1, DSM 305.10 & 292.00 panic disorder, ICD 300.01, DSM 300.01 & 300.21 anxiety, ICD 300.02, DSM 300.00 post-traumatic syndrome, DSM 309.89 memory loss, DSM 294.00 dementia of aging, ICD 290 social phobia, ICD 300.23, DSM 300.23 attention deficit hyperactivity disorder, ICD 314.0 disruptive behavior disorders, ICD 312 impulse control disorders, ICD 312, DSM 312.39 & 312.34 borderline personality disorder, ICD 301.83, DSM 301.83 chronic fatigue syndrome premature ejaculation, DSM 302.75 erectile difficulty, DSM 302.72 anorexia nervosa, ICD 307.1, DSM 307.10 disorders of sleep, ICD 307.4 autism mutism trichotillomania

Experimental Results

Representative combinations of the present invention have been tested in conscious experimental animals and the surprising results of the testing demonstrate the benefit of the invention. The tests were carried out as follows.

Microdialysis assays of monoamines

Sprague-Dawley rats (Harlan or Charles River) weighing 270–300 grams were surgically implanted with microdialysis probes under chloral hydrate/pentobarbital anesthesia (170 and 36 mg/kg i.p. in 30% propylene glycol, 14% ethanol) (Perry and Fuller, Effect of fluoxetine on serotonin and dopamine concentration in rat hypothalamus after administration of fluoxetine plus L-5-hydroxytryptophan, *Life Sci.*, 50, 1683–90 (1992)). A David Kopf stereotaxic instrument was used to implant the probe unilaterally in the hypothalamus at coordinates rostral −1.5 mm, lateral −1.3 mm, and ventral −9.0 mm (Paxinos and Watson, 1986). After a 48 hour recovery period, rats were placed in a large plastic bowl with a mounted liquid swivel system (CMA/120 system for freely moving animals, Bioanalytical Systems, West Lafayette, Ind.). Filtered artificial cerebrospinal fluid (CSF) (150 mM NaCl, 3.0 mM KCl, 1.7 mM CaCl2, and 0.9 mMMgCl2) was perfused through the probe at a rate of 1.0 μl/min. The output dialysate line was fitted to a tenport HPLC valve with a 20 μl loop. At the end of each 30 minute sampling period, dialysate collected in the loop was injected on an analytical column (Spherisorb 3 μODS2, 2×150 mm, Keystone Scientific).

The method used to measure monoamines was as described by Perry and Fuller (1993). Briefly, dialysate collected in the 20 μl loop was assayed for 5-HT, NE and DA. The 20 μl injection went onto the column with a mobile phase which resolved NE, DA, and 5-HT: 75 mM potassium acetate, 0.5 mM ethylenediaminetetraacetic acid, 1.4 mM sodium octanesulfonic acid and 8% methanol, pH 4.9. The mobile phase for the amine column was delivered with a flow programmable pump at an initial flow rate of 0.2 ml/min increasing to 0.3 ml/min at 5 min then decreasing back to 0.2 ml/min at 26 min with a total run time of 30 min. Flow programming was used to elute the 5-HT within a 25 min time period. The electrochemical detector (EG&G, Model 400) for the amine column was set at a potential of 400 mV and a sensitivity of 0.2 nA/V. The data was collected and analyzed with a Hewlett-Packard HP1000 chromatography system which measured peak heights and calculated sample concentrations. Basal levels were measured for at least 90 minutes prior to drug administration. The drugs were prepared in filtered deionized water and administered (volume 0.25–0.3 ml) at the doses stated in the results below.

Evaluation and Statistical Analyses

Extracellular levels of the amines in microdialysates were calculated by comparing peak heights with those of 50 pmole standards. The mean value of the four samples immediately preceding drug administration served as the basal level for each experiment and data was converted to percent of basal. Paired t-tests were used to compare the mean of the basal values from the time point immediately preceding drug administration to those of each time point thereafter.

The data has been rounded to make the trends more visible.

Test 1

In this test, the combination therapy comprised fluoxetine as the hydrochloride of the racemate and 4-(2-hydroxy-3-cyclohexylaminopropoxy)indole, maleate. The rats were prepared as described above, and the indole was administered subcutaneously at 3 mg/kg 100 minutes after the start of the experiment. Fluoxetine was administered intraperitoneally at 10 mg/kg, together with a second dose of the indole at 3 mg/kg, 210 minutes after the start of the experiment. Each data point reported here represents a single animal.

The 5-HT level measured in the dialysate declined upon administration of the indole, as low as about 50% of baseline, and was at about 80% of baseline at 210 minutes. It increased sharply upon administration of fluoxetine and was measured at about 410% of baseline at 240 minutes, about 450% of baseline at 270 and about 460% at 300 minutes, and at about 390% of baseline at 330 minutes.

The NE level increased upon administration of the indole, as high as about 180% of baseline, and declined nearly to baseline by 210 minutes. Upon administration of fluoxetine, it increased to about 500% of baseline at 240 minutes, and declined to about 340%, 280% and 200% of baseline at 270, 300 and 330 minutes respectively.

Similarly, DA level increased to about 210% of baseline at 120 minutes and declined to near baseline at 210 minutes. Administration of fluoxetine increased the DA level to about 1430% of baseline at 240 minutes, about 840% of baseline at 270 minutes, about 530% at 300 minutes, and about 330% at 330 minutes.

Test 2

In this test, the drugs were (+)-duloxetine, hydrochloride, administered at 4 mg/kg, and (−)-pindolol, at 5 mg/kg. The test was carried out in the same manner as Test 1, administering the (−)-pindolol first at 120 minutes after start of experiment, and then the duloxetine together with a second dose of (−)-pindolol at 5 mg/kg at 210 minutes. The results are shown below as percent of baseline of the three monoamines, at various times after the start of the experiment. Each data point represents the average of three or more animals.

| Time | 5-HT | NE | DA |
|---|---|---|---|
| 120 min. | 80% | 90% | 90% |
| 150 | 90 | 100 | 90 |
| 180 | 110 | 120 | 70 |
| 210 | 100 | 110 | 100 |
| 240 | 240 | 350 | 230 |
| 270 | 340 | 230 | 170 |
| 300 | 360 | 210 | 140 |
| 330 | — | 230 | 150 |
| 360 | 330 | 170 | 150 |

Test 3

This test was carried out as described in Test 1, using 4-(2-hydroxy-3-cyclohexylaminopropoxy)indole, maleate, at 3 mg/kg administered at 120 minutes, and (+)-duloxetine, hydrochloride, at 4 mg/kg administered with a second dose of the indole at 3 mg/kg, at 270 minutes. Results are reported as in Test 2 above. The 5-HT results are the average of three animals, and the other results are the average of four animals.

| Time | 5-HT | NE | DA |
|---|---|---|---|
| 120 min. | 90% | 100% | 70% |
| 150 | 130 | 160 | 150 |
| 180 | 130 | 140 | 130 |
| 210 | 80 | 140 | 110 |
| 240 | 90 | 130 | 100 |
| 270 | 80 | 150 | 110 |
| 300 | 650 | 580 | 410 |
| 330 | 670 | 390 | 280 |
| 360 | 590 | 450 | 240 |
| 390 | 490 | 320 | 210 |

-continued

| Time | 5-HT | NE | DA |
|------|------|-----|-----|
| 420 | 440 | 290 | 200 |

We claim:

1. A method for potentiating the action of a first component chosen from the group consisting of venlafaxine, milnacipran and duloxetine in increasing the availability of serotonin, norepinephrine and dopamine in the brain, comprising administering a first component to a patient in need thereof in combination with a second component chosen from the group consisting of alprenolol, pindolol, propranolol and tertatolol.

2. A method of claim 1 wherein the first component is duloxetine.

3. A method of claim 1 wherein the second component is pindolol.

4. A method of claim 1 wherein the availability of serotonin is increased.

5. A method of claim 3 wherein the availability of serotonin is increased.

6. A method of claim 1 wherein the second component is administered in a manner which provides a substantially constant blood level of the second component, which level is sufficient to provide a substantially constant degree of potentiation of the action of the first component.

7. A method of claim 6 wherein the first component is duloxetine.

8. A method of claim 6 wherein the second component is pindolol.

9. A method of treating a pathological condition which is created by or is dependent upon decreased availability of serotonin, norepinephrine or dopamine, which comprises administering to a patient in need of such treatment a first component chosen from the group consisting of venlafaxine, milnacipran and duloxetine, in combination with a second component chosen from the group consisting of alprenolol, pindolol, propranolol and tertatolol.

10. A method of claim 9 wherein the first component is duloxetine.

11. A method of claim 9 wherein the second component is pindolol.

12. A method of claim 9 wherein the pathological condition is depression.

13. A method of claim 9 wherein the pathological condition is obsessive-compulsive disease.

14. A method of claim 9 wherein the pathological condition is obesity.

15. A method of claim 9 wherein the pathological condition is late luteal phase syndrome.

16. A pharmaceutical composition which comprises a first component chosen from the group consisting of venlafaxine, milnacipran and duloxetine in combination with a second component chosen from the group consisting of alprenolol, pindolol, propranolol and tertatolol.

17. A composition of claim 16 which comprises duloxetine.

18. A composition of claim 16 wherein the second component is pindolol.

19. A composition of claim 16 which provides a substantially constant blood level of the second component, which level is sufficient to provide a substantially constant degree of potentiation of the action of the first component.

20. A composition of claim 19 wherein the second component is duloxetine.

21. A composition of claim 19 wherein the second component is pindolol.

* * * * *

UNITED STATES PATENT AND TRADEMARK OFFICE
CERTIFICATE OF CORRECTION

PATENT NO. : 5,532,250

DATED : July 2, 1996

INVENTOR(S) : Wong et al.

It is certified that error appears in the above-indentified patent and that said Letters Patent is hereby corrected as shown below:

Column 20, line 30,
In Claim 20 the word "second" should be the word "first".

Signed and Sealed this

Twenty-ninth Day of October 1996

Attest:

BRUCE LEHMAN

Attesting Officer     Commissioner of Patents and Trademarks